(12) United States Patent
Redano

(10) Patent No.: US 6,814,702 B2
(45) Date of Patent: *Nov. 9, 2004

(54) APPARATUS FOR MEASURING HEMODYNAMIC PARAMETERS

(75) Inventor: Richard T. Redano, Houston, TX (US)

(73) Assignee: Neutrino Development Corporation, Bellaire, TX (US)

( * ) Notice: Subject to any disclaimer, the term of this patent is extended or adjusted under 35 U.S.C. 154(b) by 299 days.

This patent is subject to a terminal disclaimer.

(21) Appl. No.: 10/134,356

(22) Filed: Apr. 27, 2002

(65) Prior Publication Data

US 2002/0138006 A1 Sep. 26, 2002

Related U.S. Application Data

(63) Continuation of application No. 09/732,274, filed on Dec. 7, 2000, now Pat. No. 6,428,478, which is a division of application No. 09/315,867, filed on May 20, 1999, now Pat. No. 6,221,021, which is a continuation-in-part of application No. 08/926,209, filed on Sep. 9, 1997, now Pat. No. 5,947,901.

(51) Int. Cl.[7] .................................................. A61B 8/06
(52) U.S. Cl. ...................................... 600/454; 600/459
(58) Field of Search ................................ 600/437, 439, 600/453–456, 459, 601

(56) References Cited

U.S. PATENT DOCUMENTS

| 3,735,756 A | 5/1973 | Richards |
| 4,246,792 A | 1/1981 | Matzuk |
| 4,334,543 A | 6/1982 | Fehr |
| 4,484,569 A | 11/1984 | Driller |
| 4,580,570 A | 4/1986 | Sarrell |
| 4,612,937 A | 9/1986 | Miller |
| 4,757,820 A | 7/1988 | Itoh |
| 5,000,185 A | 3/1991 | Yock |
| 5,062,430 A | 11/1991 | Bonnefous |
| 5,295,485 A | 3/1994 | Shinomura |
| 5,462,059 A | 10/1995 | Ferrara |
| 5,564,424 A | 10/1996 | Yao |
| 5,578,060 A | 11/1996 | Pohl |
| 5,617,864 A | 4/1997 | Stouffer |
| 5,630,837 A | 5/1997 | Crowley |
| 5,690,114 A | 11/1997 | Chiang |
| 5,692,520 A | 12/1997 | Lavoisier |
| 5,718,229 A | 2/1998 | Pesque |
| 5,722,412 A | 3/1998 | Pflugrath |
| 5,769,079 A | 6/1998 | Hossack |
| 5,785,657 A | 7/1998 | Breyer |
| 5,795,297 A | 8/1998 | Daigle |
| 5,817,024 A | 10/1998 | Ogle et al. |
| 5,851,186 A | 12/1998 | Wood et al. |
| 5,860,929 A | 1/1999 | Rubin |
| 5,871,447 A | 2/1999 | Ramamurthy |
| 5,893,363 A | 4/1999 | Little |
| 5,897,498 A | 4/1999 | Canfield |
| 6,063,034 A | 5/2000 | Doten |
| 6,221,021 B1 * | 4/2001 | Redano ..................... 600/454 |
| 6,251,076 B1 | 6/2001 | Hovland et al. |
| 6,261,233 B1 | 7/2001 | Kantorovich |

OTHER PUBLICATIONS

Mettler Electronics Brochure entitled "Sys * Stim 220" dated May 1992.
Diasonics Brochure entitled "Synergy" dated Jan. 1996.
Physio Technology Inc. Brochure entitled "Omnisound" dated 1986.
Diasonics Brochure entitled "Compact System" dated Apr. 1996.
J. D. Rainey, "Order", U.S. Dist. Ct., S.D. Tx., Civil Action No. H–01–2484, Aug. 21, 2003.

* cited by examiner

Primary Examiner—Francis J. Jaworski

(57) ABSTRACT

The present invention is directed toward an ultrasonography apparatus for measuring and/or monitoring hemodynamic activity, such as blood flow. The present invention comprises a doppler ultrasound unit, one or more transducers, and a portable body.

22 Claims, 4 Drawing Sheets

APPARATUS FOR MEASURING HEMODYNAMIC PARAMETERS

CROSS REFERENCE TO RELATED APPLICATIONS

This is a continuation of application Ser. No. 09/732,274, filed on Dec. 7, 2000 now U.S. Pat. No. 6,428,478, which is a divisional of application Ser. No. 09/315,867, filed on May 20, 1999, now U.S. Pat. No. 6,221,021, which is a continuation in part application of application Ser. No. 08/926,209, filed on Sep. 9, 1997, now U.S. Pat. No. 5,947,901.

BACKGROUND OF THE INVENTION

1. Field of The Invention

The present invention is directed toward an ultrasonography apparatus for measuring and/or monitoring hemodynamic activity, such as blood flow. The present invention comprises a doppler ultrasound unit, one or more transducers, and a portable body.

2. Description of the Prior Art

Erectile dysfunctionality may result from neurogenic, vasculogenic, hormonal, and/or psychogenic causes. The term "erectile dysfunctionality", as used herein, refers to the inability or impaired ability of a male patient to experience a penile erection. The urological arts have devised a number of therapies for treating erectile dysfunctionality. These therapies include psychological, pharmacological, and electrical therapies.

A method and device for electrically stimulating a penile erection is disclosed in U.S. Pat. No. 4,585,005 to Lue et al. The method disclosed in Lue includes the implantation of an electrode on the cavernous nerve. The electrodes of Lue are connected to a receiver that is subcutaneously implanted in the patient. The method and device disclosed in Lue requires surgery. Additionally, if the device disclosed in Lue malfunctions, surgery is required to remove it. Surgery is expensive and time consuming. Additionally, many patients may have emotional or psychological aversions to having electrodes implanted in their penis.

An apparatus for electrically stimulating penile tissue to cause a penile erection is disclosed in U.S. Pat. No. 5,571,118 to Boutos. Boutos discloses the use of a ring having a conductive surface that is placed on the penis and/or the scrotum. There is a risk that such a device may short circuit, if used in an electrically conductive environment, such as a hot tub. This is a major drawback of external electrical therapies, as contrasted with external ultrasound therapies. The use of ultrasound transducers on submerged patients has been applied in other nonanalogous arts, such as extracorporeal shock wave lithotripsy.

An apparatus for electrically stimulating a penile erection is disclosed in U.S. Pat. Nos. 4,542,753 and 4,663,102 to Brennan et al. Brennan discloses a body member for insertion into the rectum of a patient. The body member comprises surface mounted electrodes. Brennan teaches insertion of the body member sufficiently deep into the patient for at least one electrode to contact the prostate gland. The device disclosed by Brennan is highly invasive. Patients may experience physical discomfort from the rectal insertion of the device disclosed in Brennan.

Pharmacological therapies for erectile dysfunctionality include the injection of drugs into the penis. Such methods are disclosed in U.S. Pat. No. 5,236,904 to Gerstengerg et al. and U.S. Pat. No. 4,127,118 to Latorre. Many male patients find the thought of jabbing a hypodermic needle into their penis to be discomforting. Penile injections may also result in the buildup of scar tissue, bleeding, and persistent prolonged erection (priapism). The unacceptability of therapies requiring the intracavernosal injection of drugs into the penis is well documented in the urological arts (See U.S. Pat. No. 5,482,039 to Place et al. and U.S. Pat. No. 5,731,339 to Lowrey; and Padma-Nathan, *Treatment of Men With Erectile Dysfunction With Transurethral Alprostadil*, The New England Journal of Medicine, 336:1–7, Jan. 2, 1997).

Other pharmacological therapies for erectile dysfunctionality include delivering a drug directly into the urethra of a patient. Methods and devices for transurethral delivery of drugs into the penis are disclosed in U.S. Pat. Nos. 5,242,391 and 5,482,039 to Place et al. These transurethral drug delivery methods involve inserting a shaft into the urethra. The insertion of a shaft up the urethra may cause discomfort in many patients or be objectionable for many of the same reasons that penile hypodermic needle injections are objectionable.

Pharmacological agents for the treatment of erectile dysfunctionality, including vasodilators such as phosphodiesterase (PDE) inhibitors, or alpha adrenergic blockers, may also be delivered orally, transmucosally, transdermally, intranasally and/or rectally. Oral medications are available, pursuant to U.S. Food & Drug Administration (FDA) regulations, under the trademarks VIAGRA (a PDE inhibitor) from Pfizer, Inc. of New York, N.Y., and VASOMAX (an alpha adrenergic blocker) from Zonagen, Inc. of The Woodlands, Tex., or its licensees. Such oral medications are described in U.S. Pat. No. 5,731,339 to Lowrey and U.S. Pat. No. 5,565,466 to Gioco, et al.

Orally, transmucosally, transdermally, intranasally, and/or rectally ingested pharmacological agents for the treatment of erectile dysfunctionality must be dissolved into the blood stream and transported through the body to the penis. Methods of transporting such pharmacological agents to a desired site of effect, are disclosed in U.S. Pat. No. 5,565,466 and are incorporated herein, in their entirety. The time required for such pharmacological agents to be dissolved into the blood stream and transported to a site where they will relax the smooth muscle tissue in the corpora cavernosa, resulting in increased penile hemodynamic activity sufficient to cause an erection (referred to herein as the "circulatory medication response time"), can be as long as one hour. This time period can be unsatisfactory to many men and their consorts, who desire spontaneity in their sexual relations.

The present invention provides an ultrasonic therapy for hemodynamic stimulation of the penis that does not require (1) the injection of drugs into the penis, (2) surgical implantation of electrodes into the penis, or (3) the insertion of electrodes into the rectum. The method of the present invention may be used in an electrically conductive medium, such as a pool or hot tub, without the short circuiting risk present in prior art methods of electrotherapy for penile dysfunctionality. The present invention may be used to reduce the circulatory medication response time by accelerating the circulation of blood comprising a vasoactive or vasodilating agent, thereby reducing its transport time.

SUMMARY OF THE INVENTION

Blood is the hydraulic driving fluid that provides the mass increase and force which result in a penile erection. Under normal conditions, a penile erection occurs when the mass flow rate of blood into the penis exceeds the mass flow rate of blood out of the penis for a certain time interval. Vasculogenic erectile dysfunctionality may result from a restriction or blockage of blood flow into the penis or from excess blood flow out of the penis. The present invention is aimed at treating vasculogenic erectile dysfunctionality that results from inadequate blood flow into the penis.

The present invention provides a method for stimulating hemodynamic activity within a penis. The first method step of the present invention is coupling an ultrasound source to a penis. Genital lesions, such as warts or herpes simplex Type-2 lesions, can absorb and/or attenuate ultrasound thereby reducing the therapeutic effectiveness of the present invention. Accordingly, in a preferred embodiment, the ultrasound source is coupled to a lesion free region of the outer surface of a penis.

The second method step of the present invention is transmitting ultrasound energy into the corpora cavernosum of the penis at a sufficient frequency and intensity to increase hemodynamic flow within the penis. The frequency used is a function of the depth of desired penetration into the corpora cavernosum.

Initially, a frequency in the range of 2.5–3.5 MHz is desirable. As hemodynamic activity in the penis increases and the penis expands circumferentially, it is desirable to reduce the frequency of ultrasound energy from the initial frequency to a reduced frequency in the range of 1.8–2.5 MHz. The precise values of initial and reduced frequencies will be a function of the diameter of the penis being treated.

A portion of the ultrasound energy transmitted into the body is converted to thermal energy. The increased blood flow resulting from the use of the present invention provides a thermal transport medium for transporting and dispersing thermal energy introduced from the transmission of ultrasound energy. This thermal transport helps to minimize localized temperature increases within the penis. In a preferred embodiment, the ultrasound energy is emitted from one or more ultrasound transducers housed within a portable housing. Localized temperature increases can be further minimized by moving the portable housing relative to the penis being treated so as to disperse the transfer of thermal energy in the corpora cavernosum.

The present invention also provides a method for monitoring the effect of the stimulation therapy of the present invention. The present invention also includes ultrasonographically measuring one or more hemodynamic parameters within the penis. These hemdynamic parameters may include blood flow velocity, blood pressure, and/or blood temperature. The measured hemodynamic parameters can be graphically displayed to provide a real time indication of hemodynamic and/or thermal-hydraulic parameters within the penis. The measured hemodynamic parameters may be transmitted to a remote terminal for analysis by a remotely located health care professional. Alternatively, the measured hemodynamic parameters may be analyzed by an expert system located either remotely or with the patient.

The present invention is also directed toward an apparatus for stimulating hemodynamic activity within a penis. The apparatus of the present invention comprises an ultrasound generator, and a portable housing coupled to the ultrasound generator. The housing comprises at least one ultrasound trigger and a first transducer mounting assembly.

The apparatus of the present invention may also be used to ultrasonographically measure and/or display one or more hemodynamic parameters.

DESCRIPTION OF THE PREFERRED EMBODIMENTS

Figure 2:
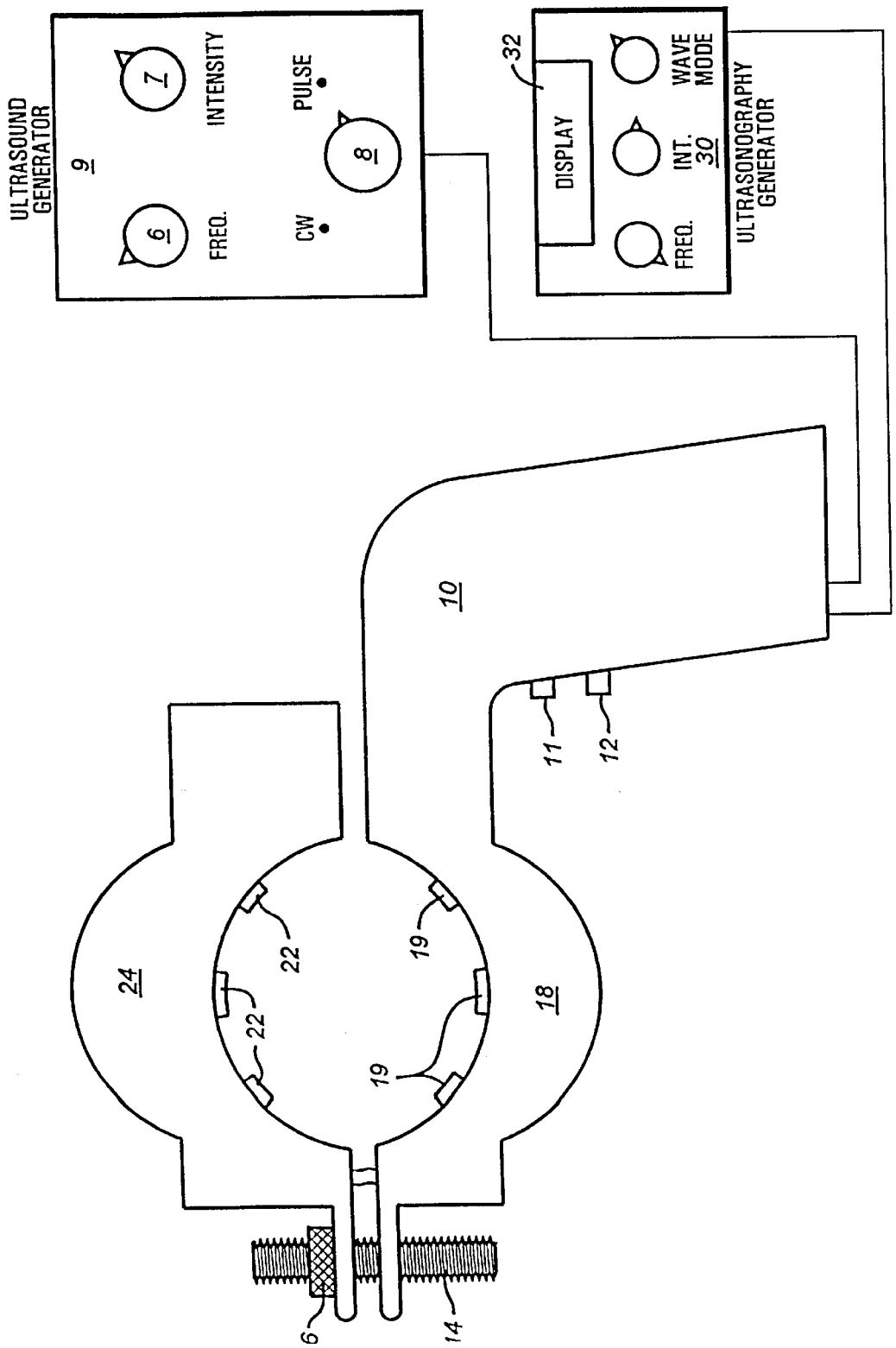
FIG. 2 is a front view of a first apparatus embodiment of the present invention.
Figure 3:
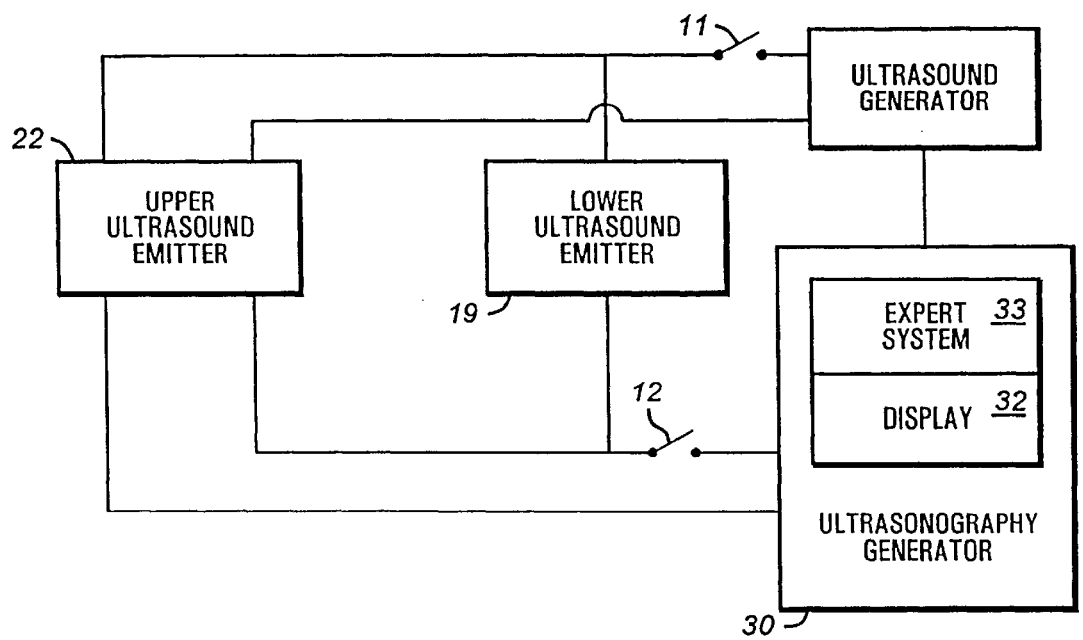
FIG. 3 is a block diagram of a second apparatus embodiment of the present invention.

The apparatus of the present invention comprises an ultrasound generator 9 and a portable housing 10 coupled to the ultrasound generator, as shown in FIG. 2. As shown in FIG. 2, control mechanisms for regulating the transmission of ultrasound energy from the ultrasound generator are mounted on body 9, which is sized to be grasped or held in a user's hand. In a preferred embodiment, these control mechanisms include knob-like fixtures 6–7 which may be adjusted to regulate or control the frequency or intensity of ultrasound energy emitted by the ultrasound generator. The portable housing comprises a fist transducer mounting assembly 18. In a preferred embodiment, the first transducer mounting assembly is curved. An ultrasound trigger 11 is mounted in the housing and is electrically coupled to the generator. The ultrasound trigger 11 is a triggering mechanism that can be actuated to cause ultrasound energy to be transmitted from the ultrasound source or emitters , as shown in FIGS. 2 and 3.

In a preferred embodiment, the ultrasound generator is capable of selectively generating pulsed or continuous wave ultrasound energy. The selective generation may be accomplished by a control knob or switch 8, as shown in FIG. 2. In a preferred embodiment, the ultrasound generator further comprises frequency controls 6 and intensity controls 7, as shown in FIG. 2. In a preferred embodiment, the ultrasound generator is capable of generating ultrasound energy within a frequency range of 1.8–3.5 MHz and within an intensity range of 1.0–2.0 watts/square centimeter.

Figure 4:
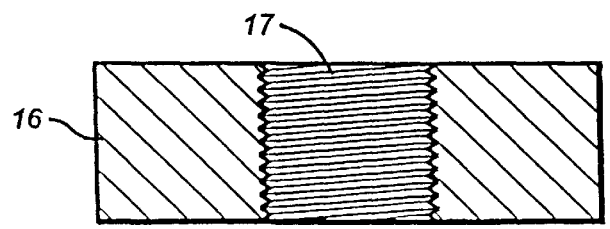
FIG. 4 is a side cross sectional view of the rotatable adjusting wheel of the present invention.

In a preferred embodiment, a position adjuster is coupled to the first transducer mounting assembly. In the preferred embodiment shown in FIGS. 2 and 4, the adjuster comprises a threaded rod 14 and a rotatable adjusting wheel 16, comprising a centrally located female threaded channel 17. The channel threadably engages the rod such that when the wheel is rotated, the rod is axially displaced.

It is known in the ultrasound arts that a satisfactory ultrasound coupling is necessary for effective delivery of ultrasound energy to a patient for therapeutic or diagnostic purposes. The position adjuster provides a mechanism for maintaining a satisfactory ultrasound coupling as the penis expands circumferentially as a result of increased hemodynamic activity. As shown in FIG. 2, the position adjuster can be used to control the separation distance between the first and second mounting assemblies, 18 and 24. The position adjuster also makes the present invention suitable for use with different patients having varied physical sizes.

The apparatus and method of the present invention may be practiced by the patient, after proper training, without assistance from another person. In the preferred embodiment shown in FIG. 2, the portable housing has a pistol type grip, thereby allowing the user to operate the trigger or triggers with one hand, while manipulating the position adjuster with the other hand, as needed to maintain a suitable ultrasound coupling during penile expansion. As shown in FIG. 2, the portable housing 10 is sized to be grasped or held in a user s hand. The placement of the triggers and axial position adjuster on opposite sides of the housing facilitates the user's ability to easily use both hands to simultaneously manipulate the trigger and the position adjuster.

In a preferred embodiment, the invention further comprises a second transducer mounting assembly 24 mounted across from the first transducer mounting assembly. As shown in FIG. 2, the position adjuster permits the distance between housing 10 and mounting assembly 24 to be adjusted by the user using one hand. In the preferred embodiment shown in FIG. 2, the mounting assembly 24 is moveably connected to the housing 10. In a preferred embodiment, the second transducer mounting assembly is mounted in alignment with the first transducer mounting assembly. In another preferred embodiment, the second transducer mounting assembly is curved. The second transducer mounting assembly is coupled to the position adjuster. In a preferred embodiment, the radii of curvature of the first and second transducer mounting assemblies are sized such that the first and second transducers can be coupled to the outer surface of a penis.

A first ultrasound emitter 19 is mounted in the first transducer mounting assembly. The first transducer is connected to the ultrasound trigger and to the ultrasound generator. Electrical and/or electronic circuitry suitable for connecting ultrasound transmitters to an ultrasound generator are described in the following U.S. Pat. Nos. 3,735,756 to Richards; 5,578,060 to Pohl et al.; and U.S. Pat. No. 4,484,569 to Driller et al. The full disclosures of these U.S. Patents is incorporated herein by reference.

A second ultrasound transducer 22 is mounted in the second transducer mounting assembly, as shown in FIG. 2. The second ultrasound emitter is connected to the ultrasound trigger and to the ultrasound generator. In a preferred embodiment, the first and second ultrasound emitters comprise a multiplicity of transducers, as shown in FIG. 2.

In the preferred embodiments shown in FIGS. 2–3, the invention further comprises an ultrasonography generator 30 connected to at least one transducer in each transducer mounting assembly and an ultrasonography trigger 12 mounted in the portable housing and connected to the ultrasonography generator. The ultrasonography trigger 12 is a triggering mechanism that can be actuated to cause ultrasound energy to be transmitted from the ultrasonography generator and through the ultrasound source or emitters, as shown in FIGS. 2 and 3. In a preferred embodiment the ultrasonography generator and the ultrasound generator are each connected to at least two ultrasound transducers in each of the transducer mounting assemblies. In a preferred embodiment the ultrasonography generator is a doppler ultrasound unit.

The ultrasonography generator is suitable for monitoring penile hemodynamic parameters, such as blood flow. Ultrasonographic apparatus suitable for use with the present invention are disclosed in the following U.S. Pat. No. 4,612,937 to Miller, and U.S. Pat. No. 4,334,543 to Fehr. The full disclosures of these two patents are incorporated herein by reference. In a preferred embodiment, the ultrasonography generator may comprise a display 32 for displaying measured hemodynamic parameters and/or expert system 33 capable of analyzing measured hemodynamic parameters. As shown in FIGS. 2 and 3, the display is located or mounted in a portable unit, such as the ultrasonography generator. As shown in FIG. 2, the ultrasonography generator unit 30 is sized to be grasped or held in a user's hand. In the preferred embodiment shown in FIG. 3, the system 33 is physically housed or located within the ultrasonography unit. In the preferred embodiment shown in FIG. 2, the ultrasonography generator unit comprises control mechanisms for regulating the transmission of ultrasound energy. In a preferred embodiment, these control mechanisms include rotatable knobs which may be adjusted to select, regulate or control the frequency, intensity or wave mode of ultrasound energy emitted by the ultrasonosgraphy generator. The expert system is capable of comparing one or more measured hemodynamic parameters to predetermined parameter limits, such as maximum blood pressure or maximum blood temperature. The expert system is further capable of generating an instruction to the user to stop ultrasound therapy if predetermined parameter limits are exceeded. These instructions may be generated via the display on the ultrasonography generator or by other visual or audible means of communication. The display of instructions stored in the expert system is an example of the ability of the display to allow the user to view stored information. In a preferred embodiment, the display 32 is centrally mounted in the top surface of the body with respect to the left and right sides of the body, as shown in FIG. 2, such that the display can be viewed by the user while grasping the body containing the ultrasonography generator. Also, in a preferred embodiment, the display 32 spans the majority of the width of the body, as shown in FIG. 2. The "wave mode" control device depicted in FIG. 2 allows for the selection of the type of ultrasound waves used by the ultrasonography generator. Typical ultrasound wave modes, as shown in FIG. 2, are continuous wave (CW) and pulsed wave (PW), or "pulse" mode. In a preferred embodiment, the ultrasonography generator may be operated in a continuous or pulsed wave mode, and the selection of such mode may be made by using the wave mode control shown in FIG. 2.

In another embodiment, the expert system is capable of generating an open circuit signal to the ultrasound generator in the event that preestablished limits are exceeded for selected hemodynamic parameters. In this embodiment, the expert system functions as a control circuit for the ultrasound generator. In a preferred embodiment, measured hemodynamic parameter data may be transmitted to a remote location by a variety of data transmission means, including telephone lines and wireless communication.

Figure 1A:
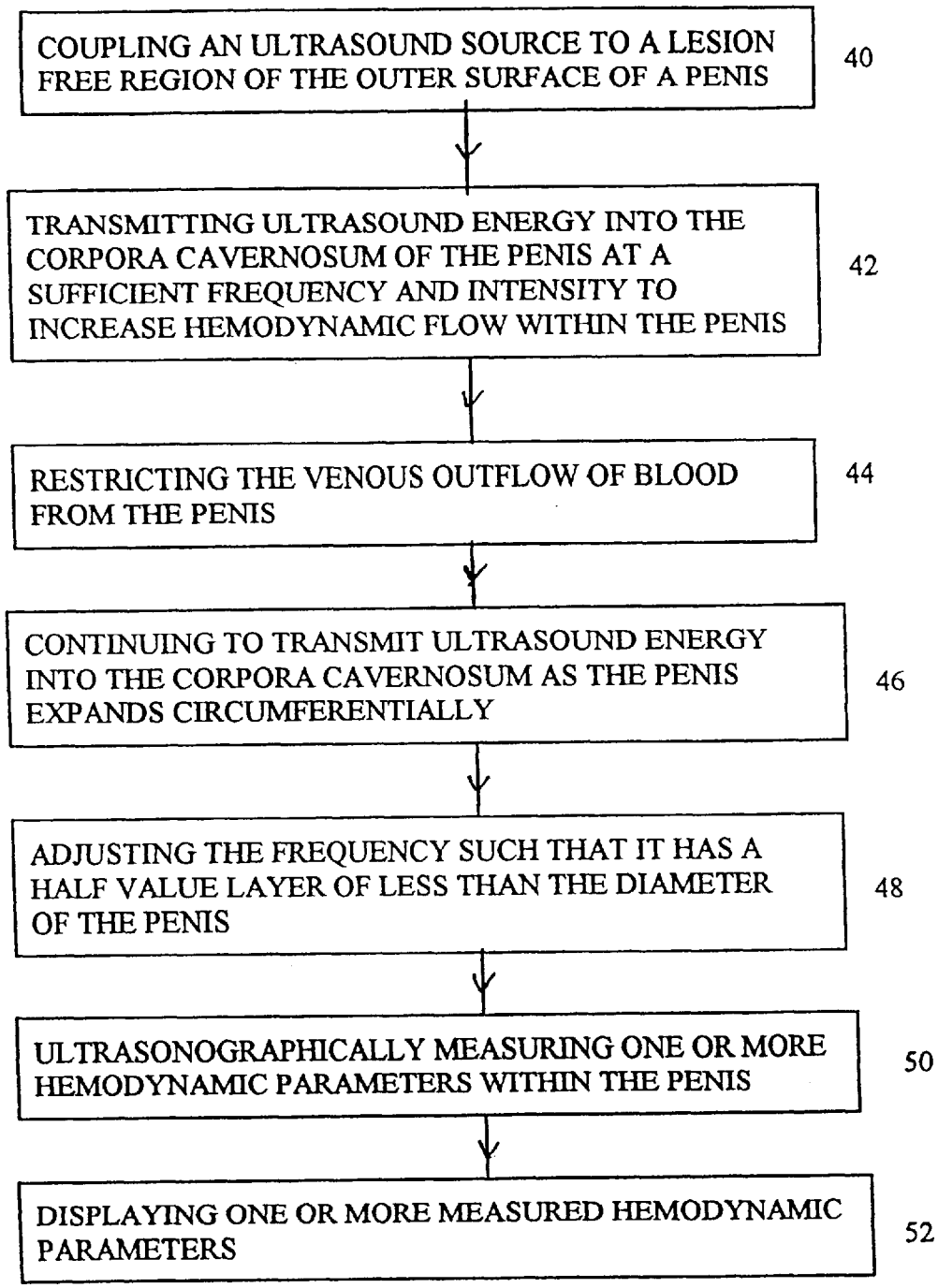
FIG. 1A is a block diagram of a first method embodiment of the present invention.
Figure 1B:
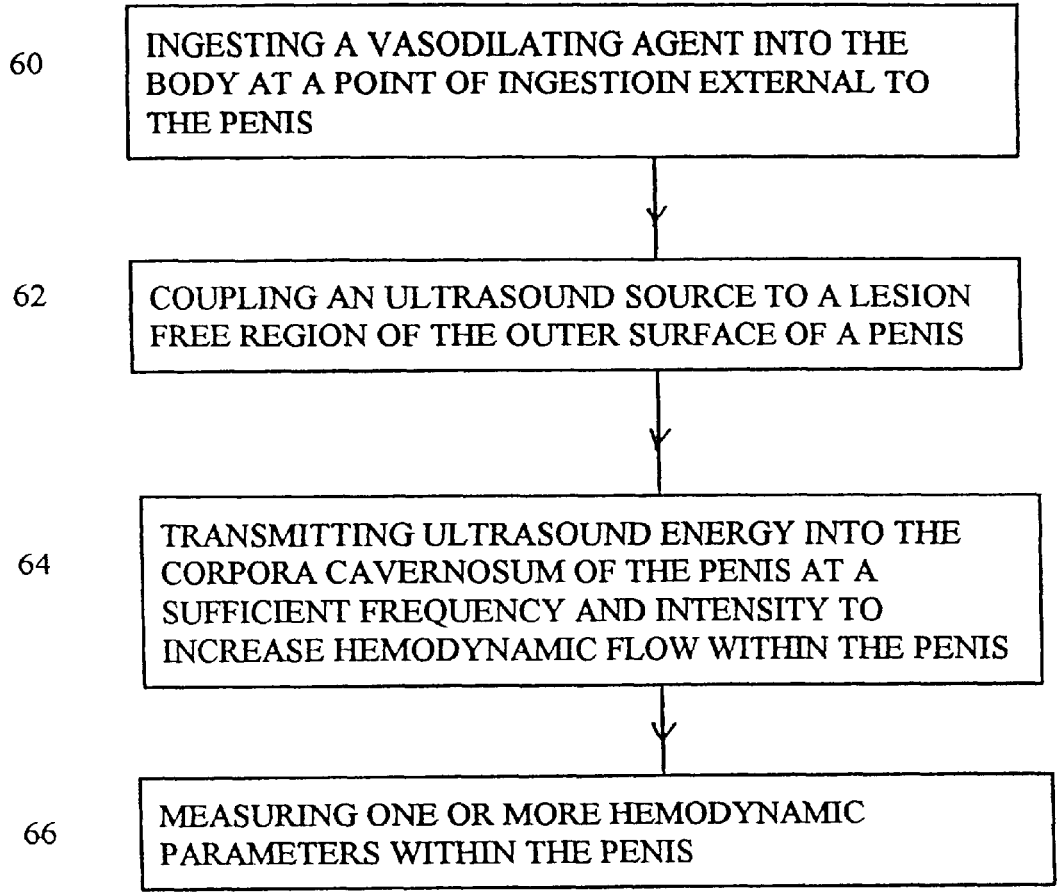
FIG. 1B is a block diagram of a second method embodiment of the present invention.

The present invention also provides a method for stimulating hemodynamic activity within a penis, as shown in FIGS. 1A–1B. The method comprises coupling an ultrasound source to the outer surface of a penis, as shown in block 40 of FIG. 1A. In a preferred embodiment the source of ultrasound energy is coupled to a lesion free region on the outer surface of the penis. In a preferred embodiment the source of ultrasound energy comprises at least two ultrasound transducers, placed on opposite sides of the penis, as shown in FIG. 2. In another preferred embodiment the source of ultrasound energy comprises a portable housing comprising the transducers.

The method further comprises transmitting ultrasound energy into the corpora cavernosum of the penis at a sufficient frequency and intensity to increase hemodynamic flow within the penis, as shown in block 42 of FIG. 1A. It is known in the ultrasound arts that 1 MHz ultrasound has a half value layer of 3.0 cm in muscle, while 3 MHz ultrasound has a half value layer of 1.0 cm in muscle. The term "half value layer", as used herein refers to the distance that ultrasound energy travels in a medium before half of the energy is absorbed. The half value layers of various ultrasound frequencies in muscle are disclosed in U.S. Pat. No. 5,413,550 to Castel. It is desirable that the frequency used be such that its half value layer will be less than the diameter of the penis being treated. In a preferred embodiment of the present invention, the frequency is adjusted such that it has a half value layer of less than the diameter of the penis being treated, as the penis expands circumferentially, as shown in blocks 46 and 48 of FIG. 1A. In a preferred embodiment, the ultrasound energy should be applied at an intensity or power density of 1.0–2.0 watts/square cm.

The transmission of ultrasound energy may be either pulsed or continuous. In a preferred embodiment the invention further comprises restricting the venous outflow of blood from the penis, as shown in block 44 of FIG. 1A.

In another preferred embodiment the invention further comprises ultrasonographically measuring one or more hemodynamic parameters within the penis, as shown in blocks 50 and 66 of FIGS. 1A and 1B, respectively. In a preferred embodiment, the ultrasonographic measuring may be performed with a doppler ultrasound unit.

In a preferred embodiment the ultrasonographic measuring comprises a measurement of blood flow velocity or blood pressure. In another preferred embodiment the transmitting and measuring steps are performed in alternating series. In a preferred embodiment, the invention further comprises displaying said measured hemodynamic parameters, as shown in block 52 of FIG. 1A.

The present invention is also directed to method for accelerating the delivery of a vasodilating agent to produce a penile erection as shown in FIG. 1B. This embodiment of the invention comprises ingesting a vasodilating agent into the body at a point of ingestion external to the penis, as shown in block 60 of FIG. 1B. In a preferred embodiment, the vasodilating agent is a PDE inhibitor or an alpha adrenergic blocker. In another preferred embodiment, the vasodilating agent is phentolamine mesylate, phentolamine hydrochloride, phenoxybenzamine yohimbine, organic nitrates, thymoxamine, imipramine, verapamil, isoxsuprine, naftidrofuryl, tolazoline, or papaverine. In a preferred embodiment the ingesting is transmucosal, transdermal, intranasal, or rectal ingesting. In another preferred embodiment, the ingesting is oral.

The invention further comprises coupling an ultrasound source to a lesion free region of the outer surface of a penis, as shown in block 62 of FIG. 1B. The invention further comprises transmitting ultrasound energy into the corpora cavernosum of the penis at a sufficient frequency and intensity to increase hemodynamic flow within the penis, as shown in block 64 of FIG. 1B.

The embodiments of the invention disclosed herein are illustrative and explanatory. Various changes in size, shape, material, as well as in the details of construction illustrated herein may be made without departing from the scope of the invention.

What is claimed is:

1. An apparatus for measuring and displaying one or more hemodynamic parameters, comprising:
   a. a portable body sized to be handheld;
   b. a doppler ultrasound unit mounted in the body;
   c. a display mounted in the body, said display being capable of displaying at least one measured hemodynamic parameter;
   d. a first transducer mounting assembly comprising at least one ultrasound transducer, wherein the mounting assembly is connected to the body such that the distance between the mounting assembly and the body can be adjusted by a user using only one hand; and
   e. a triggering mechanism connected to the doppler ultrasound unit.

2. The apparatus of claim 1, wherein the transducer mounting assembly comprises an array of ultrasound transducers.

3. The apparatus of claim 1, further comprising:
   a. a second transducer mounting assembly comprising at least one ultrasound transducer, and mounted opposite the first transducer mounting assembly;
   b. a threaded member connecting the first and second mounting assemblies; and
   c. a rotatable adjusting wheel attached to the threaded member between the first and second mounting assemblies, such that the position of one of said mounting assemblies relative to the other of said mounting assemblies can be adjusted by rotating the adjusting wheel.

4. The apparatus of claim 1, wherein the body has left and right sides and the display is centrally mounted in the surface of the body with respect to the left and right sides of the body.

5. The apparatus of claim 4, wherein the mounting assembly is connected to the body by a wire.

6. The apparatus of claim 4, wherein the triggering mechanism is connected to the transducer by a wire.

7. An apparatus for measuring and displaying one or more hemodynamic parameters, comprising:
   a. a portable body sized to be handheld;
   b. a doppler ultrasound unit mounted in the body;
   c. a display mounted in the body, said display being capable of displaying at least one measured hemodynamic parameter and said display further spanning the majority of the width of the body;
   d. a first transducer mounting assembly comprising at least one ultrasound transducer, wherein the mounting assembly is connected to the body such that the distance between the mounting assembly and the body can be adjusted by a user using only one hand; and
   e. a triggering mechanism connected to the doppler ultrasound unit.

8. The apparatus of claim 7, wherein the display is mounted in the top surface of the body.

9. The apparatus of claim 8, wherein the doppler ultrasound unit comprises a system capable of analyzing a measured hemodynamic parameter.

10. The apparatus of claim 7, further comprising:
    a. a second transducer mounting assembly comprising at least one ultrasound transducer, and mounted opposite the first transducer mounting assembly;
    b. a threaded member connecting the first and second mounting assemblies; and
    c. a rotatable adjusting wheel attached to the threaded member between the first and second mounting assemblies, such that the position of one of said mounting assemblies relative to the other of said mounting assemblies can be adjusted by rotating the adjusting wheel.

11. The apparatus of claim 7, wherein the doppler ultrasound unit is operable in a pulsed wave mode.

12. The apparatus of claim 11, wherein the doppler ultrasound unit is operable in a continuous wave mode.

13. The apparatus of claim 12, wherein the doppler ultrasound unit comprises a control device for selecting between continuous wave mode and pulsed wave mode.

14. An apparatus for a user to monitor hemodynamic parameters when the user is grasping the apparatus in one hand, comprising:
    a. a portable body sized to be grasped in a user's hand during use;
    b. a doppler ultrasound unit mounted in the body;
    c. a display mounted in the body, said display being capable of displaying at least one measured hemodynamic parameter;

d. a first transducer mounting assembly comprising at least one ultrasound transducer, wherein the mounting assembly is connected to the body such that the distance between the mounting assembly and the body can be adjusted by a user using only one hand to move the mounting assembly with respect to the body; and e. a triggering mechanism connected to the doppler ultrasound unit.

15. The apparatus of claim 14, wherein the display spans the majority of the width of the body.

16. The apparatus of claim 15, wherein the doppler ultrasound unit comprises a system capable of transmitting measured hemodynamic data to a location that is remote from said apparatus.

17. The apparatus of claim 14, wherein the doppler ultrasound unit is operable in a pulsed wave mode.

18. The apparatus of claims 17, wherein the doppler ultrasound unit is operable in a continuous wave mode.

19. The apparatus of claim 14, wherein the body comprises left and right sides, and the display is centrally mounted in the surface of the body with respect to the left and right sides of the body.

20. The apparatus of claim 14, wherein the display is mounted in the top surface of the body.

21. The apparatus of claim 14, wherein the doppler ultrasound unit comprises a system capable of analyzing a measured hemodynamic parameter and of generating an instruction to the user.

22. The apparatus of claim 14, further comprising:

a. a second transducer mounting assembly comprising at least one ultrasound transducer, and mounted opposite the first transducer mounting assembly;

b. a threaded member connecting the first and second mounting assemblies; and c. a rotatable adjusting wheel attached to the threaded member between the first and second mounting assemblies, such that the position of one of said mounting assemblies relative to the other of said mounting assemblies can be adjusted by rotating the adjusting wheel.

* * * * *